(12) United States Patent
Uhl et al.

(10) Patent No.: US 9,759,901 B2
(45) Date of Patent: Sep. 12, 2017

(54) SWITCHABLE MICROSCOPE ARRANGEMENT WITH MULTIPLE DETECTORS

(75) Inventors: Rainer Uhl, Grafelfing (DE); Rainer Daum, Wessling (DE); Xaver Voegele, Munich (DE)

(73) Assignee: FEI Company, Hillsboro, OR (US)

( * ) Notice: Subject to any disclaimer, the term of this patent is extended or adjusted under 35 U.S.C. 154(b) by 742 days.

(21) Appl. No.: 14/008,473

(22) PCT Filed: Apr. 16, 2012

(86) PCT No.: PCT/US2012/033804
§ 371 (c)(1),
(2), (4) Date: Nov. 8, 2013

(87) PCT Pub. No.: WO2012/142594
PCT Pub. Date: Oct. 18, 2012

(65) Prior Publication Data
US 2014/0160265 A1    Jun. 12, 2014

(30) Foreign Application Priority Data
Apr. 14, 2011   (DE) .................. 10 2011 017 046

(51) Int. Cl.
*G02B 21/16* (2006.01)
*G01N 21/64* (2006.01)
(Continued)

(52) U.S. Cl.
CPC ............ *G02B 21/16* (2013.01); *G01N 21/64* (2013.01); *G01N 21/6458* (2013.01); *G02B 21/361* (2013.01)

(58) Field of Classification Search
CPC ...... G02B 21/16; G02B 21/361; G02B 21/18; G02B 21/64; G02B 21/0064;
(Continued)

(56) References Cited

U.S. PATENT DOCUMENTS

| 5,412,473 A | 5/1995 | Rosencwaig et al. |
| 5,506,725 A * | 4/1996 | Koike ................ G02B 21/0072 359/368 |

(Continued)

FOREIGN PATENT DOCUMENTS

| CN | 101498833 | * 8/2009 | ............. G02B 21/00 |
| CN | 101498833 A | 8/2009 | |

(Continued)

*Primary Examiner* — Dramos I Kalapodas
(74) *Attorney, Agent, or Firm* — Scheinberg & Associates, P.C.; John E. Hillert; Michael O. Scheinberg

(57) ABSTRACT

The invention relates to a microscope arrangement provided with: a microscope (10) having at least two optical outputs (12, 14) for outputting a fluorescence signal and a switching arrangement (16) for switching the output of the fluorescence signal between the optical outputs; a beam splitter arrangement (18); optical elements (28, 30) for generating a separate partial beam path (24, 26) associated with each output in such a way that the respective fluorescence signal of each of the outputs is superimposed at the beam splitter arrangement after passing through the respective partial beam path; and also at least two optical detectors (20, 22), wherein for each of the partial beam paths, one of the detectors is located behind the beam splitter, seen from the microscope, in reflection and another of the detectors is located behind the beam splitter arrangement, seen from the microscope, in transmission.

14 Claims, 2 Drawing Sheets

(51) Int. Cl.
*G02B 21/36* (2006.01)
*G02B 21/18* (2006.01)

(58) Field of Classification Search
CPC G02B 27/1013; G02B 27/145; G02B 27/144;
G02B 21/0076; G02B 27/149; G02B
21/0012; G02B 21/22; G02B 21/365;
G02B 21/367; G02B 21/248; G02B
21/0088; G01N 21/64; G01N 21/6458;
G01N 23/223; G01N 2223/076; G01N
2015/149; G01N 15/1475; G01N
21/8851; G01N 2021/8896; G01N
2021/8829; G01N 21/65; G01N
2021/655; G01B 9/04; G01B 11/2504;
G01J 3/10; G01J 3/36; G01J 3/0243;
G01J 3/0289; G01J 3/0218; G01J 3/021;
G01J 3/02; G01J 3/0235; Y10T 436/12;
C12M 35/02; C12M 47/06; G06T 7/0065
See application file for complete search history.

(56) References Cited

U.S. PATENT DOCUMENTS

| | | | |
|---|---|---|---|
| 5,596,406 A | 1/1997 | Rosencwaig et al. | |
| 6,255,646 B1 | 7/2001 | Shimada | |
| 6,661,572 B2* | 12/2003 | Spink | G02B 21/361 |
| | | | 359/372 |
| 6,765,718 B1* | 7/2004 | Spink | G02B 21/22 |
| | | | 359/368 |
| 6,917,468 B2* | 7/2005 | Thomas | G02B 21/0044 |
| | | | 359/368 |
| 7,126,752 B2* | 10/2006 | Miyawaki | G02B 21/06 |
| | | | 359/363 |
| 7,586,674 B2* | 9/2009 | O'Connell | G02B 21/365 |
| | | | 359/368 |
| 7,961,397 B2* | 6/2011 | Marchman | H01J 37/226 |
| | | | 250/492.1 |
| 7,977,625 B2* | 7/2011 | Schwertner | G01B 11/2504 |
| | | | 250/252.1 |
| 8,040,513 B2* | 10/2011 | Uhl | G02B 17/026 |
| | | | 356/402 |
| 8,427,646 B2* | 4/2013 | Uhl | G02B 17/026 |
| | | | 356/402 |
| 2002/0024015 A1 | 2/2002 | Hoffmann et al. | |
| 2002/0041438 A1* | 4/2002 | Takahama | G02B 21/0088 |
| | | | 359/363 |
| 2002/0103439 A1* | 8/2002 | Zeng | G01J 3/0289 |
| | | | 600/476 |
| 2002/0159144 A1* | 10/2002 | Engelhardt | G02B 21/008 |
| | | | 359/385 |
| 2002/0171925 A1* | 11/2002 | Tonooka | G02B 21/248 |
| | | | 359/381 |
| 2003/0107732 A1 | 6/2003 | Sasaki et al. | |
| 2004/0114219 A1* | 6/2004 | Richardson | G01J 3/10 |
| | | | 359/368 |
| 2004/0145748 A1 | 7/2004 | Lee et al. | |
| 2005/0121596 A1* | 6/2005 | Kam | G01N 21/6458 |
| | | | 250/201.2 |
| 2007/0247630 A1 | 10/2007 | Herring | |
| 2008/0176332 A1* | 7/2008 | Berns | C12M 35/02 |
| | | | 436/55 |
| 2009/0147256 A1* | 6/2009 | Okugawa | G02B 21/32 |
| | | | 356/318 |
| 2010/0182418 A1* | 7/2010 | Jess | G02B 21/0012 |
| | | | 348/79 |
| 2012/0002030 A1* | 1/2012 | Kalkbrenner | G02B 21/16 |
| | | | 348/79 |
| 2012/0229791 A1* | 9/2012 | Lippert | G02B 21/0032 |
| | | | 356/23 |

FOREIGN PATENT DOCUMENTS

| | | | | |
|---|---|---|---|---|
| DE | 102009044987 | * | 3/2011 | G02B 21/06 |
| JP | 2005156651 | * | 6/2005 | G02B 21/06 |

* cited by examiner

SWITCHABLE MICROSCOPE ARRANGEMENT WITH MULTIPLE DETECTORS

For the observation of fluorescence signals with a microscope, cameras (CCD, sCMOS, EMCCD, ICCDs, or similar) are generally used which are connected to the microscope via outputs (ports) and optionally by additional optical elements provided for this purpose to adjust the imaging conditions or distances (relay optics). For the simultaneous observation of multiple colors, fluorescent light is often split up over multiple cameras. This can be done in the microscope, outside of the microscope, or in the camera. This color splitting is usually done depending on the wavelength or polarization through the use of dichroic elements (color splitters) in the beam path.

A general disadvantage of this arrangement for color splitting is that, in the case of the external splitting, the color splitting arrangement is available at only one port. This means in particular that the usually expensive detectors can be used only at that port. To switch a device quickly back and forth between different detection modes, such as spinning disk and wide-field or spinning disk and TIRF (total internal reflection microscopy), the disadvantage makes itself particularly felt that each configuration requires corresponding detectors and filters/filter wheels. Especially in multi-channel measurements in which one detection unit is needed per channel, significant additional costs result from the duplicate hardware.

An object of the present invention is to provide a microscope arrangement that simply and inexpensively allows a multiple use of detectors for different applications and/or through different ports.

The invention achieves this object by an arrangement in accordance with the description and claims below.

In some embodiments of the present invention, two or more detectors, such as cameras, APDs (avalanche photo detectors) or photomultipliers, are combined to allow use in different detection methods simultaneously or sequentially without reconfiguration. For this purpose, the microscope uses manual or motorized switching between different outputs, and the optical structure is preferably chosen such that the optical and/or mechanical paths of both arms are of equal or nearly equal length before the beams are superimposed again. This superimposition may be realized for example by means of a single dichroic element (color splitter or general beam splitter) or by means of a color splitter/slider or filter wheel operated manually or by a motor. This beam splitter or color splitter separates the fluorescent light again into two arms, each of which leads to one of the two detectors. Depending on the position of the switch in the microscope, the dichroic element functions for one of the two arms in transmission and for the other arm in reflection, or vice versa. Thus, two-color detection is realized for both positions of the switch.

In another embodiment of the present invention, a single optical output (port) of a microscope is used, and directly afterwards (or after relay or imaging optical element), switching occurs between the two arms with a movable mirror or other optical element (AOM (acousto-optic modulator), AOTF (acousto optical tunable filter), EOM (electro optical modulator), etc.). After optical paths of preferably equal or nearly equal lengths, the two arms are superimposed as in the aforementioned embodiment at a beam splitter (either wavelength-dependent, for example with a color separator, or independent of wavelength, for example through polarization). By this means, the configurations described in the previous example can be realized even in microscopes without an internal port switch; or a microscope where only one external port can be used may be expanded accordingly.

Figure 1:
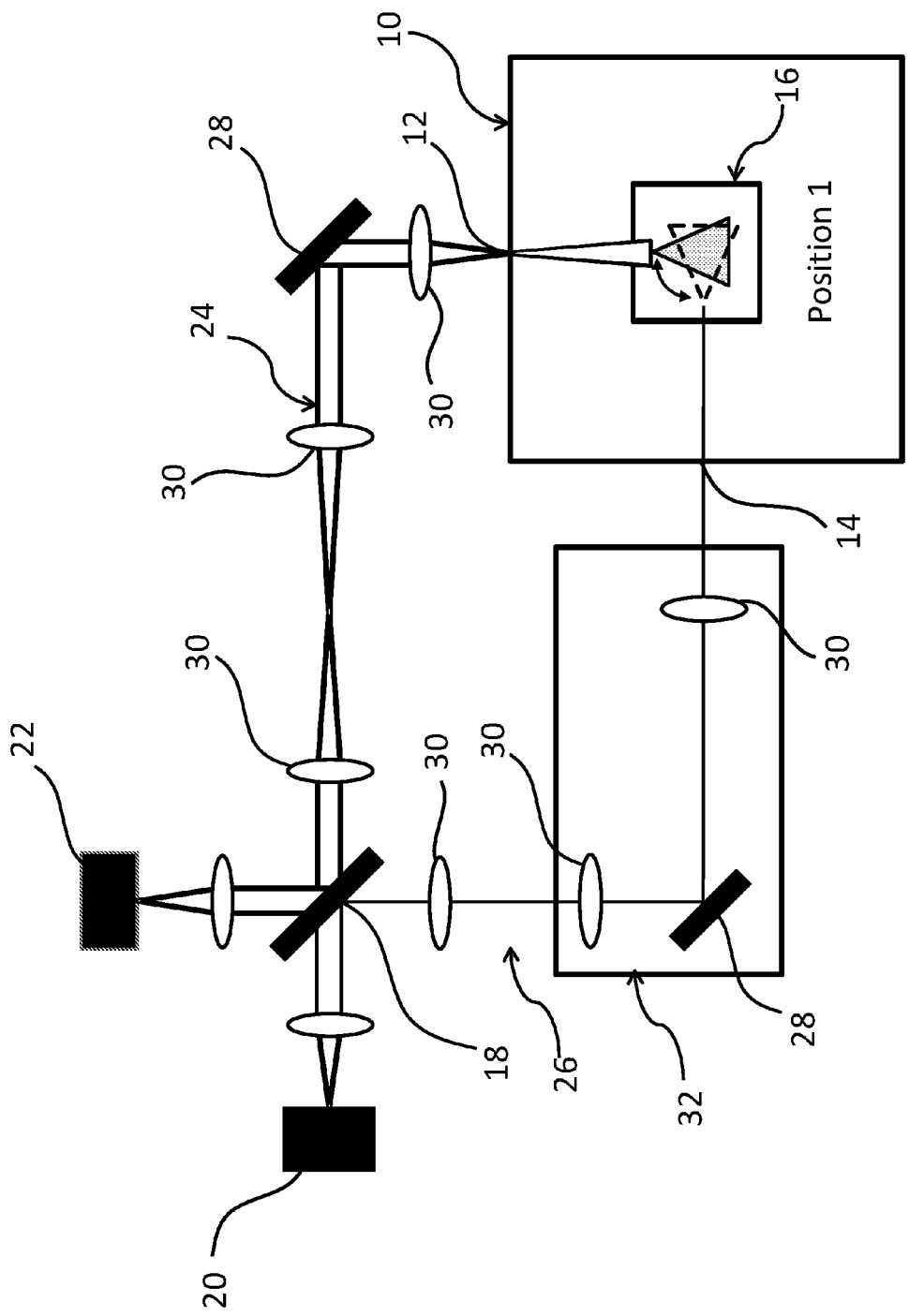
FIG. 1 shows a microscope arrangement in accordance with one embodiment of the invention.
Figure 2:
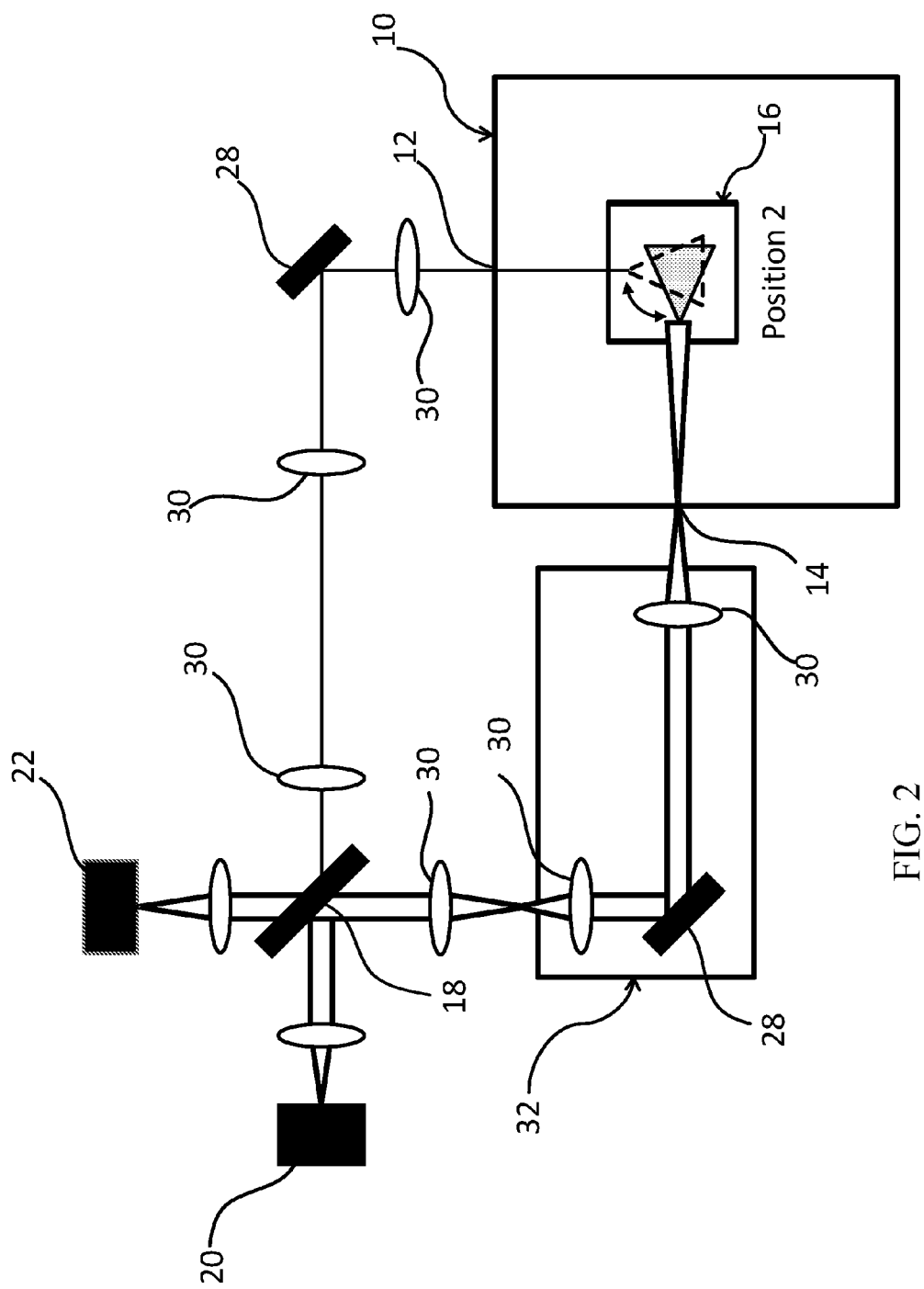
FIG. 2 shows a microscope arrangement in accordance with another embodiment of the invention.

An embodiment of the microscope arrangement of the invention is shown in FIGS. 1 and 2, which is provided with a microscope 10 having two optical outputs 12 and 14 for outputting a fluorescence signal and a switching arrangement 16 for switching the output of the fluorescence signal between the outputs 12 and 14, a beam splitter 18 configuring for example a color splitter, two optical detectors 20 and 22 as well as optical elements (mirrors 28, lenses 30) for generating two separate partial beam paths or arms 24 and 26 associated with one of the two outputs 12, 14 respectively. In the example shown, a spinning disk unit 32 (confocal Nipkov scanner) is integrated into the partial beam path 26. The partial beam paths 24, 26 are formed such that the respective fluorescence signal is superimposed at the beam splitter 18 after passing through the respective partial beam path, wherein the partial beam paths 24, 26 have an at least approximately equal-length optical path (as in example shown) or at least one of the partial beam paths is provided with an arrangement for compensation of an optical path difference (not shown). The detectors 20, 22 are arranged such that each of the partial beam paths 24 and 26, one of the detectors is behind the beam splitter 18 in reflection (seen from the microscope 10) and another of the detectors is behind the beam splitter 18 in transmission (in the example shown, for the first partial beam path 24, the detector 22 is located behind the beam splitter 18 in reflection and the detector 20 behind the beam splitter 18 in transmission, while this is exactly reversed for the second partial beam path 26).

Depending on requirements, it is possible to switch between various detection modes in the example shown. FIG. 1 shows the first position of the switch assembly 16, in which the first output 12 (and thus the first partial beam path 24) is used, which might be used for EPI (i.e., illumination and imaging beam path), TIRF-, or SI-(structured illumination) measurements. FIG. 2 shows the second position of the switching arrangement 16, in which the second output 14 (and thus the second partial beam path 26) is used, which is used for a spinning disk detection by means of the unit 32.

In an alternative embodiment, a switching arrangement corresponding to switching arrangement 16 may be provided outside of the microscope 10 in order to switch a single microscope output (for example, the output 12) between the two partial beam paths 24 and 26.

In accordance with one aspect of the invention, a microscope arrangement comprises a microscope including at least two optical outputs for outputting a fluorescence signal and a switching arrangement for switching the output of the fluorescence signal between the optical outputs; a beam splitter; optical elements for generating a separate partial beam path associated with each output in such a way that the respective fluorescence signal of each of the outputs is superimposed at the beam splitter after passing through the respective partial beam path; and at least two optical detectors, such that for each of the partial beam paths, one of the detectors is located behind the beam splitter, seen from the microscope, in reflection and another of the detectors is located behind the beam splitter, seen from the microscope, in transmission.

In some embodiments, the beam splitter comprises a color splitter. In some embodiments, at least one of the detectors comprises a camera. In some embodiments, at least one of the detectors is provided with an avalanche photo diode, a photomultiplier, or arrays thereof. In some embodiments, the switching arrangement is configured for manual switching between the outputs, or is motorized.

In accordance with another aspect of the invention, a microscope arrangement comprises a microscope having at least one optical output for outputting a fluorescence signal and a switching arrangement for switching the fluorescence signal between partial beam paths; a beam splitter; optical elements for generating partial beam paths in such a way that the fluorescence signal is superimposed at the beam splitter arrangement after passing through the respective partial beam path; and at least two optical detectors, wherein for each of the partial beam paths, one of the detectors is located behind the beam splitter, seen from the microscope, in reflection and another of the detectors is located behind the beam splitter arrangement, seen from the microscope, in transmission.

In some embodiments, the switching arrangement has an AOTF switch, an electro-optical switch, or a switch driven by a galvanometer. In some embodiments, a spinning disk unit, such as a Nipkov scanner, is integrated into one of the partial beam paths.

In some embodiments, the partial beam paths form an at least approximately equal-length optical path or at least one of the partial beam paths has an arrangement for compensation of an optical path difference.

The invention also encompasses a method of using a switchable microscope, the method comprising switching the microscope between two switchable optical outputs, the optical outputs having different optical paths, superimposing the optical output of the two optical paths at a beam splitter, and detecting the optical output using a first detector located behind the beam splitter, seen from the microscope, in reflection and a second detector located behind the beam splitter, seen from the microscope, in transmission.

In accordance with one embodiment of the method, switchable microscope is operated by switching the microscope between two switchable optical outputs, the optical outputs connecting to different optical paths; superimposing the optical output of the two optical paths at a beam splitter; and detecting the optical output using a first detector located behind the beam splitter, seen from the microscope, in reflection and a second detector located behind the beam splitter, seen from the microscope, in transmission.

In some embodiment of the method, the different optical paths of the beams are nearly equal before the beams are superimposed. In some embodiments, the method further comprises compensating for the difference in optical path lengths of the different optical outputs before the beams are superimposed. In some embodiments, superimposing the optical output of the two optical paths at a color beam splitter. In some embodiments, switching the microscope between two switchable optical outputs includes activating a switching motor.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

The invention claimed is:

1. A microscope arrangement comprising:
   a microscope, the microscope including a switching arrangement for switching a fluorescence signal between at least two optical output ports, the at least two optical output ports including a first optical output port and a second optical output port;
   a beam splitter;
   a first plurality of optical elements configured to provide a first beam path from the first optical output port to the beam splitter and a second plurality of optical elements configured to provide a second beam path from the second optical output port to the beam splitter, the optical elements of the first and second pluralities arranged such that the first beam path and the second beam path converge at the beam splitter; and
   at least two optical detectors, the at least two optical detectors including a first optical detector and a second optical detector arranged with respect to the beam splitter such that:
   when the fluorescence signal is transmitted along the first beam path, the portion of the fluorescence signal passing through the beam splitter is received by the first optical detector and the portion of the fluorescence signal reflected by the beam splitter is received by the second optical detector, and
   when the fluorescence signal is transmitted along the second beam path, the portion of the fluorescence signal passing through the beam splitter is received by the second optical detector and the portion of the fluorescence signal reflected by the beam splitter is received by the first optical detector,
   wherein the switching arrangement is configured to:
   divert the fluorescence signal from the first beam path to the second beam path by redirecting the fluorescence signal inside the microscope away from the first optical output port and toward the second optical output port; and
   divert the fluorescence signal from the second beam path to the first beam path by redirecting the fluorescence signal inside the microscope away from the second optical output port and toward the first optical output port.

2. The microscope arrangement of claim 1, in which the beam splitter comprises a color splitter.

3. The microscope arrangement of claim 1, in which at least one of the detectors comprises a camera.

4. The microscope arrangement of claim 3 in which at least one of the detectors is provided with an avalanche photo diode, a photomultiplier, or arrays thereof.

5. The microscope arrangement of claim 1, in which the switching arrangement is configured for manual switching between the optical output ports, or is motorized.

6. A microscope arrangement comprising:
   a microscope having at least one optical output port for outputting a fluorescence signal;
   a beam splitter;

optical elements arranged to provide a first beam path and a second beam path, the optical elements arranged such that the ends of the first beam path and the second beam path converge at the beam splitter;

a switching arrangement comprising an acousto-optic tunable filter (AOTF) switch, an electro-optical switch, a switch driven by a galvanometer, a movable mirror having two arms, an acousto-optic modulator (AOM), or an electro optical modulator (EOM), and configured to:
- divert the fluorescence signal from the first beam path to the second beam path by redirecting the fluorescence signal inside the microscope away from the first optical output port and toward the second optical output port, and
- divert the fluorescence signal from the second beam path to the first beam path by redirecting the fluorescence signal inside the microscope away from the second optical output port and toward the first optical output port;

at least two optical detectors, the at least two optical detectors including a first optical detector and a second optical detector arranged with respect to the beam splitter such that:
- when the fluorescence signal is transmitted along the first beam path, the portion of the fluorescence signal passing through the beam splitter is received by the first optical detector and the portion of the fluorescence signal reflected by the beam splitter is received by the second optical detector, and
- when the fluorescence signal is transmitted along the second beam path, the portion of the fluorescence signal passing through the beam splitter is received by the second optical detector and the portion of the fluorescence signal reflected by the beam splitter is received by the first optical detector.

7. The microscope arrangement of claim 6, in which the switching arrangement is motorized.

8. The microscope arrangement of claim 6 in which a spinning disk unit (Nipkov scanner) is integrated into one of the beam paths.

9. The microscope arrangement of claim 6, in which the beam paths are approximately equal in length or at least one of the beam paths has an arrangement to compensate for a difference in length between the first beam and the second beam path.

10. A method of operating a switchable microscope having a first optical output connecting to a first optical path and a second optical output connecting to a second optical path, the downstream ends of the first optical path and the second optical path converging at a beam splitter disposed outside the switchable microscope, the method comprising:
- generating a fluorescence signal within the switchable microscope,
- outputting the fluorescence signal from the switchable microscope to the first optical path by directing the fluorescence signal inside the switchable microscope towards the first optical output;
- transmitting the fluorescence signal along the first optical path and through the beam splitter, such that:
  - a first portion of the fluorescence signal is transmitted through the beam splitter and detected by a first detector located by the beam splitter, and
  - a second portion of the fluorescence signal is reflected by the beam splitter and detected by a second detector located behind the beam splitter;
- outputting the fluorescence signal from the switchable microscope to the second optical path by diverting the fluorescence signal from the first optical output to the second optical output using a switching arrangement configured to redirect the path of the fluorescence signal inside the switchable microscope;
- transmitting the fluorescence signal along the second optical path and through the beam splitter, such that:
  - a first portion of the fluorescence signal is transmitted through the beam splitter and detected by the second detector, and
  - a second portion of the fluorescence signal is reflected by the beam splitter and detected by the first detector.

11. The method of claim 10 in which the first optical path and the second optical path are nearly equal in length.

12. The method of claim 10 further comprising compensating for a difference in length between the first optical path and the second optical path.

13. The method of claim 10 in which the beam splitter comprises a color beam splitter.

14. The method of claim 10 in which diverting the fluorescence signal from the first optical output to the second optical output includes activating a switching motor of the switching arrangement.

* * * * *